United States Patent [19]
Ritz et al.

[11] Patent Number: 5,782,841
[45] Date of Patent: Jul. 21, 1998

[54] TUNNELING TOOL FOR SUBCUTANEOUS LEAD PLACEMENT

[75] Inventors: James A. Ritz, Lenexa, Kans.; Brian L. Fideler, Columbia Heights, Minn.

[73] Assignee: Medtronic, Inc., Minneapolis, Minn.

[21] Appl. No.: 104,965

[22] Filed: Aug. 10, 1993

[51] Int. Cl.$^6$ ........................................... A61B 17/00
[52] U.S. Cl. ................................... 606/129; 606/1
[58] Field of Search ........................ 128/639, 642, 128/419 P, 899; 606/1, 129; 607/36, 119, 131

[56] References Cited

U.S. PATENT DOCUMENTS

| | | |
|---|---|---|
| 4,010,757 | 3/1977 | Jula . |
| 5,036,854 | 8/1991 | Schollmeyer et al. ............. 128/642 |
| 5,170,787 | 12/1992 | Lindegren ............................ 128/642 |
| 5,241,957 | 9/1993 | Camps et al. ........................ 607/119 |
| 5,300,106 | 4/1994 | Dahl et al. ........................... 607/119 |

OTHER PUBLICATIONS

MEDTRONIC Model 3464 Receiver/Extension Internalization Manual, SE–4 For Spinal Cord Stimulation (SCS), 1978.

*Primary Examiner*—Glenn K. Dawson
*Attorney, Agent, or Firm*—Reed A. Duthler; Harold R. Patton

[57] ABSTRACT

A tunneling tool for subcutaneous lead placement which includes a carrier capsule and a tunneling rod. The capsule has a bottom section and a hinged cover section which together provide an enclosure to confine the connectors on one or more leads. The capsule is provided with a latching mechanism and is opened by manually deflecting the bottom section to release the latching mechanism. The capsule is provided with a releasable catch at the forward end thereof for pivotally attaching the capsule end of a tunneling rod.

8 Claims, 2 Drawing Sheets

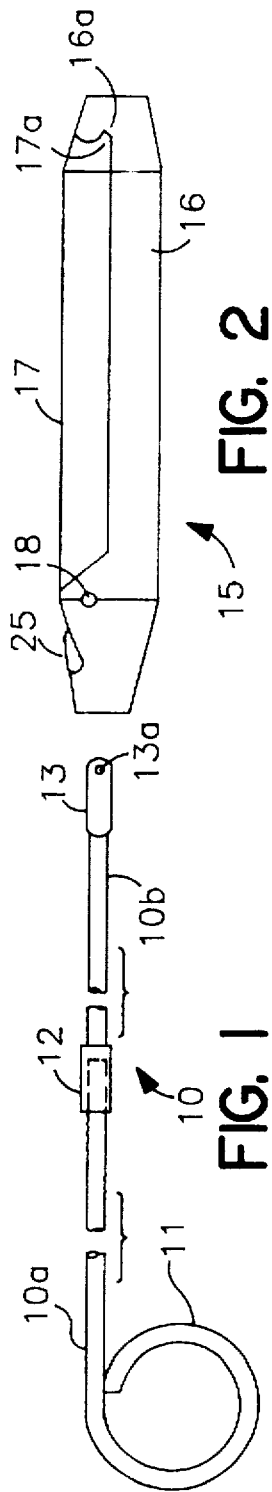

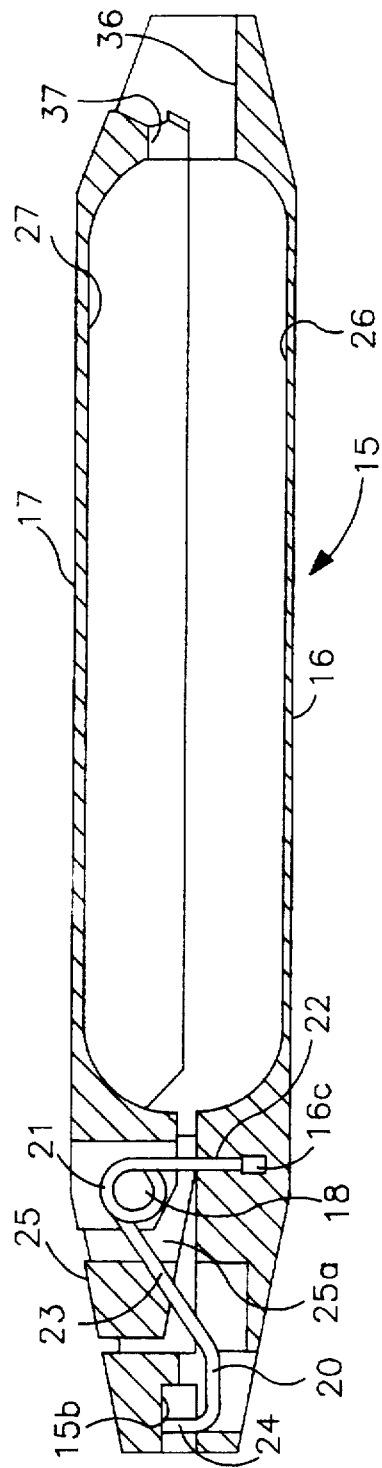
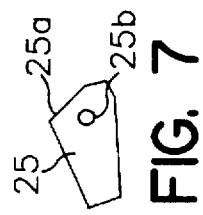
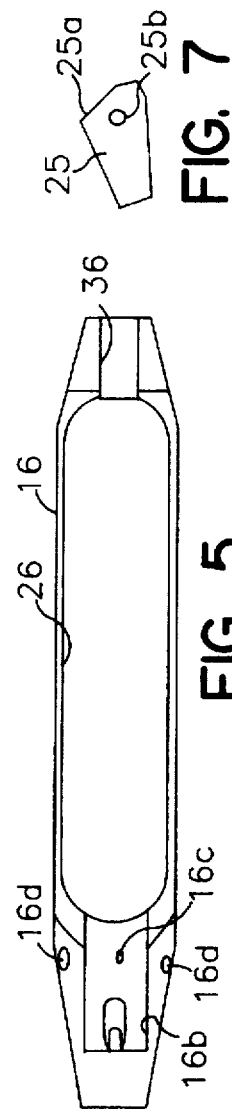
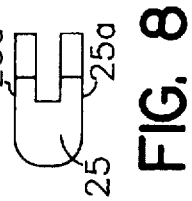
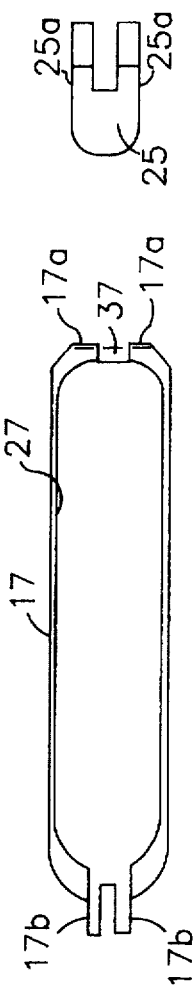

5,782,841

TUNNELING TOOL FOR SUBCUTANEOUS LEAD PLACEMENT

BACKGROUND OF THE INVENTION

This invention relates generally to the field of implantable medical devices and more particularly to surgical tools for assisting in the implant of such devices.

In some applications of implantable stimulators, the site of implant of the stimulator is remote from the site of the associated stimulation electrodes. For example, when epicardial pacing electrodes are employed in conjunction with an implanted cardiac pacemaker, the leads exit the thoracic cavity adjacent the heart, and extend subcutaneously to the pacemaker, which may be located subcutaneously in the abdominal or pectoral region. Similarly, subcutaneous tunneling of electrical leads between the implant site of the pulse generator and the electrode site is often required in conjunction with the implant of pacemaker/cardioverter/ defibrillators. A tool for assisting in passing pacing leads subcutaneously is disclosed in U.S. Pat. No. 4,010,757. The tunneling tool includes a receptacle for the connector pin of the lead and is pushed through the subcutaneous tissue with the lead trailing behind. In this case, the electrode, mounted to the lead, is first implanted at its desired location and the lead is thereafter tunneled to the pulse generator implant site.

Subcutaneous tunneling of leads is also often required in conjunction with implantable nerve and muscle stimulators. One example of a tool for use in implanting such devices is the Medtronic Subcupass tunneling tool, which includes a carrier for the connector end of a lead, and which is pulled through the subcutaneous tissue with the lead trailing behind it. In this case, the electrodes are implanted first and the lead, coupled to the pulse generator is tunneled from the pulse generator implant site to the electrode implant site.

SUMMARY OF THE INVENTION

The present invention is intended to provide a subcutaneous tunneling tool which will transport leads and connectors subcutaneously with minimal trauma and injury to the subcutaneous tissue and also with minimal risk of damage or contamination to the leads.

The tunneling tool embodying the invention includes a capsule which provides an enclosure cavity to receive and enclose one or more lead connectors attached to ends of respective leads. A hinged capsule cover is initially opened to permit the lead connectors to be placed in the cavity and the cover is then snapped shut to enclose the connectors therein. The lead connectors are thus completely enclosed during tunneling, protecting them from damage and contamination during the tunneling procedure.

The tool also includes a tunneling rod which is first passed subcutaneously along the desired path for the leads. The capsule is then attached to a tunneling rod, by means of a push button operated spring catch to permit subcutaneous transport of the capsule by pulling the rod back through the subcutaneous tissue with the capsule and leads trailing behind. The spring catch of the capsule is designed to allow defection of the capsule relative to the tunneling rod, easing its passage through the tissue. The capsule is provided with tapered end portions, which also assist in passage of the capsule through the subcutaneous tissue.

DESCRIPTION OF THE DRAWINGS

FIG. 1 is a side plan view of the tunneling rod;

FIG. 2 is a side plan view of the capsule assembly;

FIG. 3 is side view showing the method of opening the capsule;

FIG. 4 is an enlarged, cut-away view of the capsule;

FIG. 5 is a top plan view of the capsule bottom section;

FIG. 6 is a bottom plan view of the capsule top section;

FIG. 7 is a side plan view of the release button for operating the spring catch of the capsule; and FIG. 8 is a top plan view of the release button for operating the spring catch of the capsule.

DETAILED DESCRIPTION OF THE PREFERRED EMBODIMENT OF THE INVENTION

FIG. 1 is a side view of the tunneling rod 10. The tunneling rod 10 is constructed of two sections 10a and 10b which are connected by an internally threaded connector sleeve 12. Section 10a has a gripping loop 11 and section 10b is provided with a flattened attachment portion 13 having a connecting hole 13a therethrough for connection with the spring catch in the capsule.

FIG. 2 is a side view of the capsule 15. The capsule 15 includes a bottom or base section 16 and a hinged top or cover section 17 which together provides an internal compartment for enclosing the lead ends and connectors to be transported. Capsule top section 17 pivots around hinge pin 18. Capsule top section 17 is provided with two latch projections 17a, which snap into latch recesses 16a on capsule base section 16, to maintain the capsule top section 17 in a closed position. Button 25, which releases the spring catch of the capsule is also visible.

FIG. 3 illustrates the manner in which the capsule is opened. The material from which the two sections 16 and 17 are manufactured is sufficiently resilient to permit bending the capsule when gripped between the thumbs and index fingers of the two hands of the surgeon, as illustrated. The capsule is bent along its longitudinal axis into a "banana" shape by pushing the thumbs upward, which in turn pops the latch projections 17a out of the latch recesses 16a of the bottom section 16. "Delrin" plastic is a suitable material for providing this resiliency and the other properties required for surgical instruments. "Delrin" is manufactured by DuPont who also owns the Trademark Registration for the mark.

FIG. 3 shows the capsule in cut-away view, illustrating the relationship of the capsule top and base sections 17, 16, the release button 25, the hinge pin 18 and the spring catch 20.

The capsule top and bottom sections 17 and 16 are provided with internal recesses 27 and 26, respectively, which together define an enclosure for the connectors of the leads to be tunneled. The rearward ends of the top and bottom sections 17 and 16 are provided with grooves 37 and 36, respectively, which together define on opening through which the leads pass. The dimensions of the grooves 36, 37 should be chosen such that they are large enough to permit passage of the lead bodies, but smaller than the dimensions of the connectors, so that the leads will be retained when the capsule is closed.

Spring catch 20 includes a coil spring section 21 mounted around hinge pin 18 and a stabilizing anchor section 22, extending down into an anchor hole 16c formed in the forward end portion of the base section 16. A spring arm 23 extends forwardly from spring coil 21 within the nose portion of the bottom section 16. The forward end of the base section 16 has a recess formed therein in which release button 25 is mounted. The release button 25 has rearwardly extending spaced mounting ears 25a which are pivotally mounted on the hinge pin 18 with spring arm 23 disposed therebetween. Release button 25 engages the upper surface of spring arm 23.

A hitch pin 24 is formed at the front end of the spring arm 23 and is moved downwardly into retracted position by applying downward pressure to the release button 25 which depresses the arm 23 and pin 24. The forward end of the capsule 15 is provided with a front hitch opening 15b in which the flattened hitch portion 13 (FIG. 1) of the tunneling rod is inserted after release button 25 is depressed to displace the hitch pin 24. Connecting hole 13a of the tunneling rod is then aligned with the pin 24, and the release button is allowed to move upward, so that hinge pin 24 passes through the connecting hole 13a, to couple the capsule and rod together. The internal vertical and horizontal dimensions of the front hitch opening 16b are greater the corresponding outer dimensions of the flattened portion 13 of the tunneling rod and the connecting hole 13a has a larger diameter than the hitch pin 24. These factors, taken together, allow the capsule to pivot freely in both vertical and horizontal axes, with respect to the tunneling rod. The ability of the capsule to pivot, along with the tapered ends of the capsule, assist in easing its passage through the subcutaneous tissue.

Once connected to the capsule 15, the tunneling rod 10 can then be used as a tow bar to pull the capsule 15 with the leads and lead connectors therein down through the subcutaneous path previously defined by the tunneling rod when the rod was pushed through the subcutaneous tissue. When the leads have been drawn down into their desired location, the release button 25 is depressed to release hitch pin 24 from the tunneling rod 10 and the capsule 15 is opened by applying axial bending force thereto to snap the cover section 17 into open position and the leads and connectors are then removed from the capsule and attached as appropriate.

FIG. 5 is a top plan view of capsule bottom section 16. Recess 26, groove 36, and hole 16c, are all discussed above. The recess 16b in which the release button 25 is mounted is also illustrated, along with bores 16d, for receiving the hinge pin 18.

FIG. 6 is a bottom plan view of capsule top section 17. recess 26, groove 36 and latch projections 17a are all discussed above. Also illustrated are the two ears 17b, which are provided with bores through which hinge pin 18 passes to pivotally mount the top section 17.

In conjunction with the above specification, we claim:
What is claimed is:

1. A tool for use in the placement of implantable leads, comprising:

a capsule having a forward end, a rearward end and an internal cavity, said internal cavity open to the rearward end of said capsule comprising first and second longitudinally extending sections pivotally mounted to one another at a pivot point, said first section fabricated of a material which may be deformed manually, said capsule further provided with latch means spaced from said pivot point for mechanically latching said first and second sections to one another and for mechanically unlatching said first and second sections from one another in response to manual deformation of said first section between said pivot point and said latch means.

2. A tool according to claim 1 wherein said latch means comprises a longitudinally extending projection on one of said first and second sections and a corresponding recess on the other of said first and second sections.

3. A tool according to claim 1 wherein said internal cavity lies between said pivot point and said latch means.

4. A tool according to claim 1 wherein said pivot point is located adjacent said forward end of said capsule.

5. A tool for use in the placement of implantable leads, comprising:

a capsule having a forward end, a rearward end and an internal cavity, said internal cavity open to the rearward end of said capsule, said capsule comprising first and second longitudinally extending sections pivotally mounted to one another at a pivot located adjacent only said forward end, said first section fabricated of a material which may be deformed manually, said capsule further provided with latch means located adjacent only said rearward end, for mechanically latching said first and second sections to one another and for mechanically unlatching said first and second sections from one another in response to manual deformation of said first section between said pivot point and said latch means.

6. A tool according to claim 5 wherein said internal cavity lies between said pivot point and said latch means.

7. A tool according to claim 5 wherein said forward end of said capsule tapers to a reduced cross section.

8. A tool according to claim 5 or claim 6 or claim 7, further comprising means for removably mounting said capsule to a tunnelling rod, located at the forward end of said capsule.

* * * * *